(12) United States Patent
Dib et al.

(10) Patent No.: US 6,380,208 B2
(45) Date of Patent: Apr. 30, 2002

(54) USE OF NICERGOLINE FOR TREATING SPASTICITY

(75) Inventors: Michel Dib; Vincent Meininger, both of Paris (FR)

(73) Assignee: Aventis Pharma S.A., Anthony Cedex (FR)

( * ) Notice: Subject to any disclaimer, the term of this patent is extended or adjusted under 35 U.S.C. 154(b) by 0 days.

(21) Appl. No.: 09/863,787

(22) Filed: May 23, 2001

Related U.S. Application Data

(63) Continuation of application No. PCT/FR99/02866, filed on Nov. 22, 1999.

(30) Foreign Application Priority Data

Nov. 24, 1998 (FR) .............................. 98 14794

(51) Int. Cl.⁷ ..................... A61K 31/44; A61K 31/425
(52) U.S. Cl. ........................ 514/288; 514/367
(58) Field of Search ................... 514/288, 367

(56) References Cited

U.S. PATENT DOCUMENTS

| | | | |
|---|---|---|---|
| 3,228,943 | A | 1/1966 | Bernadi et al. |
| 6,297,254 | B1 * | 10/2001 | Dib et al. |

FOREIGN PATENT DOCUMENTS

| | | |
|---|---|---|
| DE | 4240798 | 6/1993 |
| EP | 0050551 | 9/1981 |
| EP | 0602619 | 6/1994 |
| JP | 06016555 | 1/1994 |

OTHER PUBLICATIONS

Chem. Abstracts, vol. 107, 228784x (1987).
Chem. Abstracts, vol. 118, 225224f (1993).
Chem. Abstracts, vol. 105, 54314k (1986).
Chem. Abstracts, vol. 113, 52358u (1990).
Chem. Abstracts, vol. 111, 108396h (1989).
Chem. Abstracts, vol. 109, 86208c (1988).
Chem. Abstracts, vol. 106, 12788h (1987).
Chem. Abstracts, vol. 115, 198237s (1991).
J. Takahashi, et al: BR. *J. Phramacol.*, vol. 100, pp. 705–710 (1990).
M. Tanaka, et al: *Neuroscience Letters*, vol. 248 pp. 68–72 (1998).
P. Castaigne, et al: *Revue Neurol.*, vol. 127, pp. 401–414 (1972).
C. Carpene, et al: *J. Pharmacol.*(Paris), vol. 14 (1), pp. 57–66, (1983).
Sanderink G. J.,et al: *Journal of Pharmacology and Experimental Therapeutics*, vol. 282 (3) pp. 1465–1472, (1997).
Martinet M., et al: *Drugs of Today*, vol. 33 (8), pp. 587–594, (1997).
O. Elwan, et al: *Journal of International Medical Research*, vol. 23 (3), pp.154–166, (1995).

* cited by examiner

*Primary Examiner*—William R. A. Jarvis
*Assistant Examiner*—Vickie Kim
(74) *Attorney, Agent, or Firm*—Balaram Gupta

(57) ABSTRACT

The invention concerns the use of nicergoline for treating pyramidal spasticity of neurological diseases involving a pathology of the cerebrospinal tract.

18 Claims, No Drawings

USE OF NICERGOLINE FOR TREATING SPASTICITY

This application is a continuation of International application No. PCT/FR99/02,866, filed Nov. 22, 1999; which claims the benefit of priority of French Patent Application No. 98/14,794, filed Nov. 24, 1998.

The present invention relates to the use of nicergoline in the treatment of the pyramidal spasticity of neurological diseases involving an attack of the pyramidal pathway.

Spasticity is among the clinical traits of neurological diseases which have in common an attack of the pyramidal pathway, such as, for example, amyotrophic lateral sclerosis, progressive spinal muscular atrophy, infantile muscular atrophy, primary lateral sclerosis and cerebrovascular accidents.

Nicergoline, or (8β)-10-methoxy-1,6-dimethyl-ergoline-8-methanol-5-bromonicotinate (Sermion®), in particular has α-blocking and (α2-adrenolytic properties (CARPENE C. et al., J. Pharmacol, 14, 57–66 (1983)), anti-ischemic properties (CAHN R. et al., Chem. Abstracts, 107, 228784x (1987); UEDAT et al., Chem. Abstracts, 118, 225224f (1993)), anti-calcium properties (TAKAHASHI K. et al., Br. J. Pharmacol., 100, 705–710 (1990)), antioxidant properties (TANAKA M. et al., Neurosci. Let., 248, 67–72 (1998)) and antithrombotic properties (Chem. Abstracts 105, 54314k (1986)). It improves the memory and the learning capacity (Chem. Abstracts, 113, 52358u (1990); Chem. Abstracts, 111, 108396h, 1989; Chem. Abstracts, 109, 86208c, 1988; Chem. Abstracts, 106, 12788e, 1987; Chem. Abstracts, 115, 198237s, 1991).

It has now been found that nicergoline reduces the pyramidal spasticity of neurological diseases involving an attack of the pyramidal pathway and, in particular, of the spasticity during amyotrophic lateral sclerosis, progressive spinal muscular atrophy, infantile muscular atrophy, primary lateral sclerosis and cerebrovascular accidents.

Amyotrophic lateral sclerosis (ALS), also known as Charcot's disease and Lou Gehrig's disease, was described for the first time by Charcot in 1865. ALS is a fatal disease resulting from degeneration of the motor neurones. The disease is accompanied by a progressive paralysis, leading to the loss of the motor and respiratory functions and then to death within a period of two to eight years from the appearance of the first symptoms.

Stiffness is among the characteristic clinical traits of this condition. Its degree is variable and it is common to find that there are very stiff patients opposite patients who have little or no stiffness.

This stiffness is generally related to hypertonia (or contracture or spasticity) of the pyramidal syndrome and it is common to consider it as being due to the exclusive attack of the pyramidal pathway.

Clinically, however, it is not always easy to relate the stiffness observed to pyramidal attack alone.

The reason for this is that it is necessary to distinguish between pyramidal stiffness (or contracture or spasticity) and extrapyramidal stiffness (or rigidity).

Pyramidal contracture (increase in the motor tonus, known as Ch. Foix tendon reflexes) is clinically elastic, it becomes reinforced as the muscular insertion points become separated and it is exaggerated with the speed of movement of the limb and gives the mobilized limb a primitive attitude. It predominates on the flexors in the upper limbs and on the extensors in the lower limbs, with a predominance on the distal muscles.

Extrapyramidal rigidity (exaggeration of the Ch. Foix "posturereflex" plastic tonus), on the other hand, is a sensation of waxy elastic resistance, which is attenuated by repeated gentle passive mobilization. It affects all muscles, predominantly the proximal (rhizomelic) muscles. The tonus of the limbs is exaggerated during passive shortening of the muscle defining the over excitation of the Ch. Foix posture reflexes (Strümpell's fixing rigidity). It tends to fix the limb in the position in which the observer has set it. In this respect, it is similar to phenomena of catatonia and catalepsy.

Finally, these changes in tonus should be combined with oppositional rigidity or Gegenhalten's rigidity which more reflects a frontal attack. It is similar to extrapyramidal rigidity, but differs therefrom by its fluctuating nature and by its exaggeration when the patient attempts to relax.

A certain amount of data argues in favor of attack of the extrapyramidal system in patients suffering from ALS.

In addition to the known association of ALS and Parkinson's disease (in particular in Guam's anatomo-clinical complex), various anatomo-clinical studies have objectivized an attack of the central grey matter. As early as 1925, I. Bertrand and L. Van Bogaert (Rev. Neurol., 32, 779–806 (12925)) reported a diffuse attack of the cerebral cortex and of the central grey matter in patients suffering from ALS. In 1972, P. Castaigne et al. (Rev. Neurol., 127, 401–414 (1972)) noted an attack of the central grey matter in 16 out of 19 "atypical" cases of ALS, although there did not appear to be any clinical extrapyramidal signs in these patients. Isolated cases of ALS with attack of the substantia nigra have also been reported (S.M. Chou, Dekker pub. pp. 133–181 (1992)). By means of a PET scan with 6-fluorodopa, Takahashi et al. (J. Neural. Transm., 5, 17–26 (1993)) showed a decrease in the uptake of fluorodopa in all patients, despite the absence of a clear clinical sign of attack of the extrapyramidal system. This decrease appears to be accentuated gradually over time in the course of the disease.

Clinical experience shows that most stiff patients have a mixed stiffness: pyramidal and extrapyramidal. An important argument in favor of a probably mixed origin of the stiffness observed in patients suffering from ALS is that this symptom is inaccessible or relatively inaccessible to the muscular relaxant treatments usually used in pyramidal spasticity (baclofen, benzodiazepines and dantrolene).

The distinction between rigidity and spasticity is not only of descriptive importance, but is also of importance in the treatment of these patients. The reason for this is that stiffness is a factor that is probably "favorable" in the vital prognosis, but definitely "unfavorable" in the functional prognosis since it is inaccessible or relatively inaccessible to the usual muscular relaxants, even at the price of a considerable increase in doses (occasionally 180 mg/day of baclofen).

A descriptive study on 9 patients suffering from ALS was carried out. The main criterion defined is the stiffness, measured using a visual analog scale (VAS), of 100 mm, or the individual rates by self-assessment the severity of the stiffness perceived.

To date, only riluzole (2-amino-6-trifluoro-methoxybenzothiazole) is sold, under the name Rilutek®, for the treatment of amyotrophic lateral sclerosis. Riluzole mainly makes it possible to slow down the progression of the disease, but has no effect on the spasticity.

The patients receive 100 mg/day of riluzole and 15 mg IV of nicergoline on the first day and 30 mg IV on the next 4 days. The duration of infusion was more than 4 hours to avoid any risk of hypotension.

The measurement was carried out before and after administration of nicergoline.

The results are as follows (mean±standard deviation, in mm):

The stiffness before administration of nicergoline is 67.33±25.

The stiffness 4 days later (from 4 to 8 d) is 48.11±19.

The intra-individual difference is 19.22±20.5 (95% I=3.44+35; range=−8 to +57).

The comparison at a zero difference is significant (t=2.809; p (2 α)=0.0229).

The test of deviation from a normal distribution is non-significant.

The present application also relates to the combination of riluzole or a pharmaceutically acceptable salt of riluzole and of nicergoline, and to its use in the treatment of the pyramidal spasticity of neurological diseases involving an attack of the pyramidal pathway and, in particular, of spasticity during amyotrophic lateral sclerosis, progressive spinal muscular atrophy, infantile muscular atrophy, primary lateral sclerosis and cerebrovascular accidents.

The nicergoline may be prepared according to U.S. Pat. No. 3,228,943.

The riluzole may be prepared according to the process disclosed in EP Patent No. 50551.

Pharmaceutically acceptable salts of riluzole which may be mentioned in particular include the addition salts with mineral acids such as hydrochloride, sulfate, nitrate or phosphate, or with organic acids such as acetate, propionate, succinate, oxalate, benzoate, fumarate, maleate, methanesulfonate, isethionate, theophillineacetate, salicylate, phenolphthalinate and methylenebis-β-oxynaphthoate, or substitution derivatives of these derivatives.

The nicergoline may be used orally, parenterally or rectally.

The combination of nicergoline and riluzole may be used orally, parenterally or rectally, either simultaneously or separately or sequentially over time.

The present invention also relates to pharmaceutical compositions comprising nicergoline in pure form or in the form of a combination with one or more compatible and pharmaceutically acceptable diluents and/or adjuvants and/or optionally in combination with another pharmaceutically compatible and physiologically active product and optionally in combination with riluzole or a pharmaceutically acceptable salt thereof.

Solid compositions for oral administration which may be used include tablets, pills, powders (gelatin capsules or cachets) and granules. In these compositions, the active principles are mixed with one or more inert diluents, such as starch, cellulose, sucrose, lactose or silica, under a stream of argon. These compositions may also comprise substances other than diluents, for example one or more lubricants such as magnesium stearate or talc, a colorant, a coating (sugar coating) or a varnish.

Liquid compositions for oral administration which may be used include pharmaceutically acceptable solutions, suspensions, emulsions, syrups and elixirs containing inert diluents such as water, ethanol, glycerol, plant oils or liquid paraffin. These compositions may comprise substances other than diluents, for example wetting, sweetening, thickening, flavoring or stabilizing products.

The sterile compositions for parenteral administration may preferably be aqueous or non-aqueous solutions, suspensions or emulsions. Solvents or vehicles which may be used include water, propylene glycol, a polyethylene glycol, plant oils, in particular olive oil, injectable organic esters, for example ethyl oleate, or other suitable organic solvents. These compositions may also contain adjuvants, in particular wetting agents, isotonic agents, emulsifiers, dispersants and stabilizers. The sterilization may be carried out in several ways, for example by aseptic filtration, by incorporating sterilizing agents into the compositions, by irradiation or by heating. They may also be prepared in the form of sterile solid compositions which may be dissolved at the time of use in sterile water or any other injectable sterile medium.

The compositions for rectal administration are suppositories or rectal capsules which contain, in addition to the active product, excipients such as cocoa butter, semi-synthetic glycerides or polyethylene glycols.

The present invention also relates to the use of nicergoline either alone or in combination with riluzole or a pharmaceutically acceptable salt thereof, for the preparation of medicinal products that are useful in the treatment of the pyramidal spasticity of neurological diseases involving an attack of the pyramidal pathway, and in particular of amyotrophic lateral sclerosis, progressive spinal muscular atrophy, infantile muscular atrophy, primary lateral sclerosis and cerebrovascular accidents.

The present invention also relates to the method for treating the pyramidal spasticity of neurological diseases involving an attack of the pyramidal pathway, and in particular of amyotrophic lateral sclerosis, progressive spinal muscular atrophy, infantile muscular atrophy, primary lateral sclerosis and cerebrovascular accidents, which consists in administering to the, patient nicergoline or a combination of nicergoline and riluzole or a pharmaceutically acceptable salt thereof, either simultaneously or separately or sequentially over time.

The doses depend on the desired effect, the duration of the treatment and the route of administration used; they are generally from 15 to 30 mg per day orally for an adult, with unit doses of from 5 to 10 mg of nicergoline.

When the combination of nicergoline and riluzole is used, the doses are generally from 10 to 400 mg per day orally for an adult, with unit doses ranging from 10 to 200 mg of riluzole and from 15 to 30 mg per day orally for an adult, with unit doses of from 5 to 10 mg of nicergoline.

In general, the doctor will determine the appropriate dosage depending on the age and weight and all the other factors specific to the individual to be treated.

What is claimed is:

1. A method for the treatment of the pyramidal spasticity of neurological diseases involving an attack of the pyramidal pathway comprising administering to a patient in need thereof a pharmaceutical composition consisting of at least about 5 mg of nicergoline and at least about 10 mg of riluzole or a pharmaceutically acceptable salt thereof, optionally in combination with a pharmaceutically acceptable carrier.

2. The method as claimed in claim 1 in which the spasticity of the neurological diseases involving an attack of the pyramidal pathway is tie spasticity of amyotrophic lateral sclerosis.

3. The method as claimed in claim 1 in which the spasticity of the neurological diseases involving an attack of the pyramidal pathway is the spasticity of progressive spinal muscular atrophy.

4. The method as claimed in claim 1 in which the spasticity of the neurological diseases involving an attack of the pyramidal pathway is the spasticity of infantile muscular atrophy.

5. The method as claimed in claim 1 in which the spasticity of the neurological diseases involving an attack of the pyramidal pathway is the spasticity of primary lateral sclerosis.

6. The method as claimed in claim 1 in which the spasticity of the neurological diseases involving an attack of the pyramidal pathway is the spasticity of cerebrovascular accidents.

7. The method as claimed in claim 1 wherein said amount of riluzole and said amount of nicergoline are administered simultaneously.

8. The method as claimed in claim 1 wherein said amount of riluzole and said amount of nicergoline are administered sequentially.

9. The method as claimed in claim 1 wherein said administration of riluzole and nicergoline is spaced out over time.

10. The method as claimed in claim 1 wherein the pharmaceutical composition contains 5 to 10 mg of nicergoline and 10 to 200 mg of riluzole.

11. The method as claimed in claim 2 wherein the pharmaceutical composition contains 5 to 10 mg of nicergoline and 10 to 200 mg of riluzole.

12. The method as claimed in claim 3 wherein the pharmaceutical composition contains 5 to 10 mg of nicergoline and 10 to 200 mg of riluzole.

13. The method as claimed in claim 4 wherein the pharmaceutical composition contains 5 to 10 mg of nicergoline and 10 to 200 mg of riluzole.

14. The method as claimed in claim 5 wherein the pharmaceutical composition contains 5 to 10 mg of nicergoline and 10 to 200 mg of riluzole.

15. The method as claimed in claim 6 wherein the pharmaceutical composition contains 5 to 10 mg of nicergoline and 10 to 200 mg of riluzole.

16. A pharmaceutical composition comprising at least about 5 mg of nicergoline and at least about 10 mg of riluzole or a pharmaceutically acceptable salt thereof optionally in combination with a pharmaceutically acceptable carrier, useful in the treatment of the pyramidal spasticity of neurological diseases involving an attack of the pyramidal pathway.

17. The composition as claimed in claim 16 which contains 5 to 10 mg of nicergoline and 10 to 200 mg of riluzole.

18. The composition as claimed in claim 16, as a combined preparation for simultaneous, separate or sequential use.

* * * * *